(12) United States Patent
Yodfat et al.

(10) Patent No.: US 6,740,105 B2
(45) Date of Patent: May 25, 2004

(54) EXPANDABLE DELIVERY APPLIANCE PARTICULARLY FOR DELIVERING INTRAVASCULAR DEVICES

(75) Inventors: Ofer Yodfat, Modi'in (IL); Avi Rapaport, Tel Aviv (IL)

(73) Assignee: Mind Guard Ltd., Caesarea (IL)

( * ) Notice: Subject to any disclaimer, the term of this patent is extended or adjusted under 35 U.S.C. 154(b) by 0 days.

(21) Appl. No.: 10/288,472

(22) Filed: Nov. 6, 2002

(65) Prior Publication Data

US 2003/0100939 A1 May 29, 2003

Related U.S. Application Data

(60) Provisional application No. 60/332,057, filed on Nov. 23, 2001.

(51) Int. Cl.[7] .............................................. A61M 29/00
(52) U.S. Cl. ...................................................... 606/198
(58) Field of Search ................................ 606/192–199, 606/108; 604/150

(56) References Cited

U.S. PATENT DOCUMENTS

| | | | |
|---|---|---|---|
| 4,950,227 A | | 8/1990 | Savin et al. |
| 5,108,370 A | | 4/1992 | Walinsky |
| 5,108,416 A | | 4/1992 | Ryan et al. |
| 5,232,446 A | | 8/1993 | Arney |
| 5,275,610 A | * | 1/1994 | Eberbach ................... 606/198 |
| 5,549,613 A | | 8/1996 | Goble et al. |
| 5,634,928 A | | 6/1997 | Fischell et al. |
| 5,649,906 A | * | 7/1997 | Gory et al. .................. 606/108 |
| 5,713,907 A | * | 2/1998 | Hogendijk et al. .......... 606/198 |
| 6,221,043 B1 | | 4/2001 | Fischell et al. |
| 6,245,040 B1 | | 6/2001 | Inderbitzen et al. |

FOREIGN PATENT DOCUMENTS

EP 0364420 B1 11/1992

* cited by examiner

Primary Examiner—Kevin T. Truong
(74) Attorney, Agent, or Firm—G.E. Ehrlich (1995) Ltd.

(57) ABSTRACT

A delivery appliance for delivering an expandable annular device, particularly an expandable intravascular device, to a desired location in a lumen, includes an annular array of supporting strips extending from a proximal end of the annular array to a distal end of the annular array, to define an annular supporting surface for the expandable annular device. Each of the supporting strips is laterally deformable to radially expand or radially contract the annular array and the annular supporting surface defined thereby. A connecting stem passes through the annular array of supporting strips and has a distal end coupled to the supporting strips at the distal end of the annular array for axial movement therewith, and a proximal end passing through the proximal end of the annular array of supporting strips for axial movement with respect thereto. The proximal end of the connecting stem is axially movable in opposite directions to move the distal end of the annular array axially away from or towards, the proximal end of the annular array to radially contract or radially expand the annular supporting surface.

25 Claims, 10 Drawing Sheets

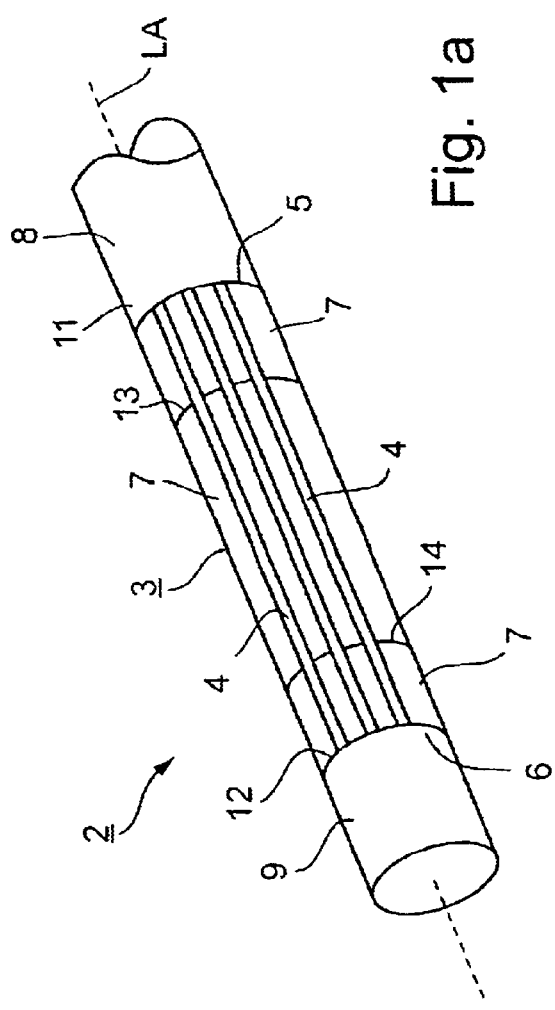
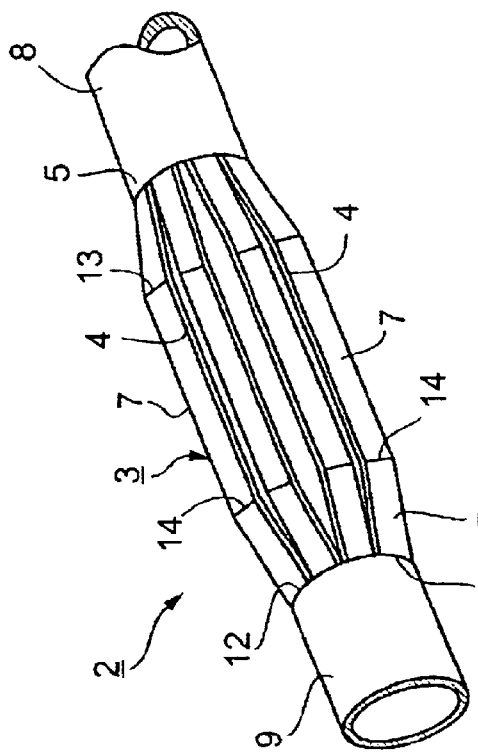

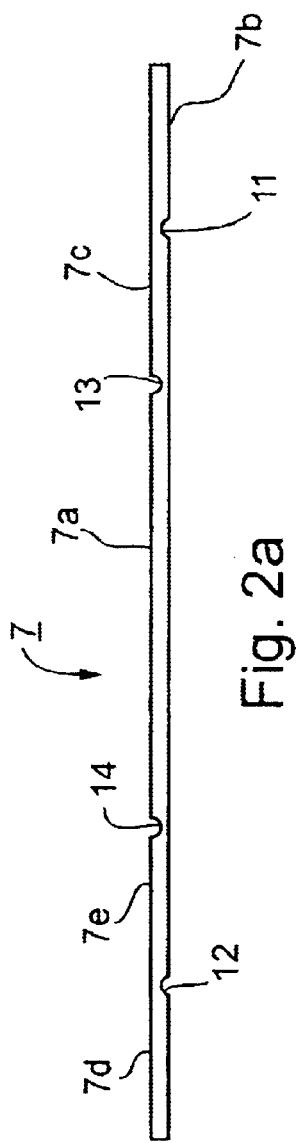
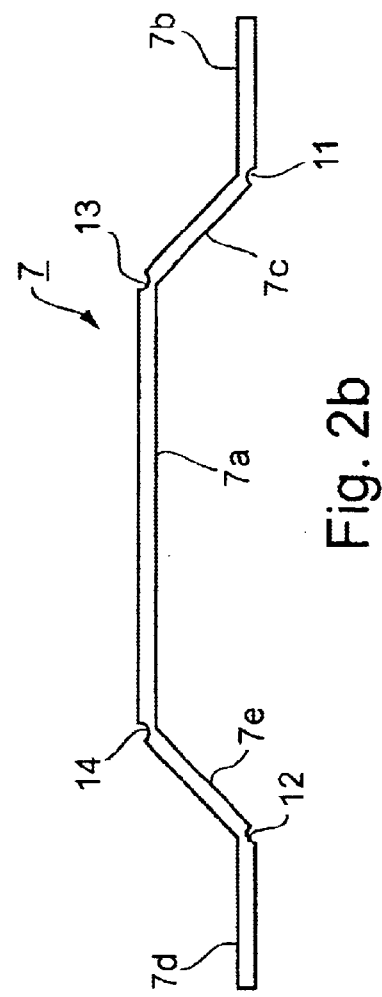
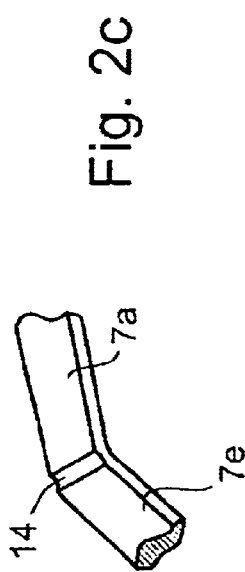

EXPANDABLE DELIVERY APPLIANCE PARTICULARLY FOR DELIVERING INTRAVASCULAR DEVICES

RELATED PATENT APPLICATION

This application claims the benefit of U.S. Provisional Application No. 60/332,057 filed Nov. 23, 2001.

FIELD AND BACKGROUND OF THE INVENTION

The present invention relates to delivery appliances for delivering an expandable annular device to a desired location in a lumen. The invention is particularly useful in medical applications, for delivering an expandable intraluminal device, especially an intravascular device, to a desired location in the lumen of a subject's body, and is therefore described below with respect to such an application.

Numerous types of implantable intravascular devices, such as stents, grafts, sensors, and filters are well known in the prior art. Also well known are delivery systems and methods for guiding these devices to the proper location within the body and for deploying them at the desired location, as described, for example, in U.S. Pat. Nos. 6,221,043; 4,950,227; 5,634,928; 5,108,416; and 5,549,613. Such delivery systems typically include balloon-type catheters, in which the balloon is deflated to receive the intravascular device and to deliver it to the desired location, and then inflated to expand the intravascular device and thereby to press it firmly against the walls of the lumen. After the intravascular device has been so deployed, the balloon is again deflated in order to remove the catheter from the lumen, leaving the intravascular device deployed within the lumen.

However, in the type of deployment procedure disclosed in these patents, the balloon, when completely expanded, blocks the lumen during the procedure of implanting the device, and thereby prevents the flow of blood. This can be extremely hazardous or even fatal.

Perfusion balloon catheters, which permit partial flow of bodily fluids such as blood past an inflated balloon, are also well known in the art and are use for angioplasty. In this type of catheter, the balloon is formed such that, when inflated within a bodily cavity, one or more channels are provided for the flow of bodily fluids or blood past the inflated balloon. Perfusion balloon catheters are generally not used for implanting intraluminal devices, but rather for the opening of a stenotic artery as a part of the Percutaneous Transluminal Angioplasty (PTA) procedure. When the balloon in a perfusion flow system is inflated, the central part of the lumen is blocked as in the other systems of the prior art, but a small channel is provided, usually in the form of a helix, between the expanded balloon and the wall of the lumen. Typical perfusion balloon catheter systems are disclosed, for example, in U.S. Pat. Nos. 6,245,040; 5,108,370; and 5,232,446.

In some situations, for example in the deployment of self-expandable intraluminal devices in the aortic arch or in the intracranial arteries, the complete blockage of the lumen by the balloon during the implantation process, even for a short period of time, may also be highly hazardous or even fatal.

Another drawback in the use of a conventional balloon catheter for self-expanding intervascular devices is the danger of over inflation, which can cause significant damage to the intimal and the medial layers of the vessel wall, and increased restenosis of the intervascular devices. The use of a conventional balloon catheter in a large diameter vessel, such as the aorta, may also be problematical because of the difficulty of expanding the balloon to the large size required for this application with sufficient force to anchor the intravascular device in place without damaging the vessel walls.

OBJECTS AND BRIEF SUMMARY OF THE INVENTION

An object of the present invention is to provide a delivery appliance, which is not based on an inflatable balloon, for delivering an expandable annular device to a desired location in a lumen. Another object is to provide a delivery appliance for delivering an expandable intraluminal device, particularly an intravascular device, to a desired location in a lumen of the vascular system of the subject's body, which delivery appliance does not have the foregoing disadvantages of an inflatable-balloon type delivery appliance when used for such applications.

According to a broad aspect of the present invention, there is provided a delivery appliance for delivering an expandable annular device to a desired location in a lumen, comprising: an annular array of supporting strips extending from a proximal end of the annular array to a distal end of the annular array, to define an annular supporting surface for the expandable annular device, each of the supporting strips being laterally deformable to radially expand or radially contract the annular array and the annular supporting surface defined thereby; and a connecting stem passing through the annular array of supporting strips; the connecting stem having a distal end coupled to the supporting strips at the distal end of the annular array for axial movement therewith., and a proximal end passing through the proximal end of the annular array of supporting strips for axial movement with respect thereto; the proximal end of the connecting stem being axially movable in one direction to move the distal end of the annular array axially away from the proximal end of the annular array to radially contract the annular supporting surface; the proximal end of the connecting stem being axially movable in the opposite direction to move the distal end of the annular array axially towards the proximal end of the annular array to radially expand the annular supporting surface.

According to further features in the preferred embodiments of the invention described below, each of the supporting strips in the annular array is stiff in the longitudinal direction, but is formed with at least one integral hinge to permit its deformation in the lateral direction. More particularly, each of the supporting strips includes a strip of stiff material extending from the proximal end of the annular array to the distal end of the annular array and formed with at least one transversely-extending groove producing the at least one integral hinge. The transversely-extending groove is formed on one surface of the strip of stiff material to permit the strip to be laterally deformed more easily in the direction of that surface than in the opposite direction.

According to further features in the preferred embodiments of the invention described below, each of the supporting strips in the annular array is formed with at least one integral hinge at the proximal end of the annular array, and with at least one integral hinge at the distal end of the annular array, such that the intermediate portions of the supporting strips remain substantially parallel to the longitudinal axis of the annular array during the radial contraction and the radial expansion of the annular supporting surface defined by the supporting strips. In the described preferred embodiments, each of the supporting strips in the annular array is formed with two integral hinges at the proximal end of the annular array, and with two integral hinges at the distal end of the annular array.

According to still further features in the preferred embodiments of the invention described below, the delivery appliance further includes an outer sleeve receiving the annular array of supporting strips when the annular array is in its contracted condition to maintain them in its contracted condition until the outer sleeve is removed from the annular array of supporting strips. The expandable annular device is interposed between the outer sleeve and the annular array of supporting strips when the annular array is in its contracted condition.

In one described preferred embodiment, the proximal end of the stem, and the proximal end of the annular array of supporting strips, are both extended outwardly in the proximal direction to enable the proximal ends of the stem and of the annular array of supporting strips to be manually grasped in order to effect the axial movement in the one direction or in the opposite direction.

In a second described preferred embodiment, a spring is interposed between the proximal end of the stem and the proximal end of the annular array of supporting strips urging the proximal ends apart, such that removal of the outer sleeve causes the spring automatically to effect the axial movement in the opposite direction to expand the inner supporting surface and thereby the annular device supported thereon.

It will thus be seen that such a delivery appliance eliminates the need for an inflatable balloon, and therefore avoids many of the problems and difficulties, as described above, associated with such inflatable balloons. This make the delivery appliance particularly useful in medical applications for delivering intraluminal devices, especially intravascular devices.

Further features and advantages of the invention will be apparent from the description below.

BRIEF DESCRIPTION OF THE DRAWINGS

The invention is herein described, by way of example only, with reference to the accompanying drawings, wherein:

FIG. 1a is a perspective view illustrating the expendable part in one form of delivery appliance constructed in accordance with the invention, the expendable part being shown in its contracted state;

FIG. 1b is a perspective view showing the expendable part of the delivery appliance of FIG. 1 in its expanded state;

FIG. 2a is a side view illustrating one of the supporting strips in the delivery appliance of FIGS. 1a and 1b;

FIG. 2b is a side view illustrating the supporting strip of FIG. 2a in the expanded state of the appliance;

FIG. 2c is a fragmentary view illustrating one of the integral hinges in the supporting strip of FIG. 2a;

Figure 3A:
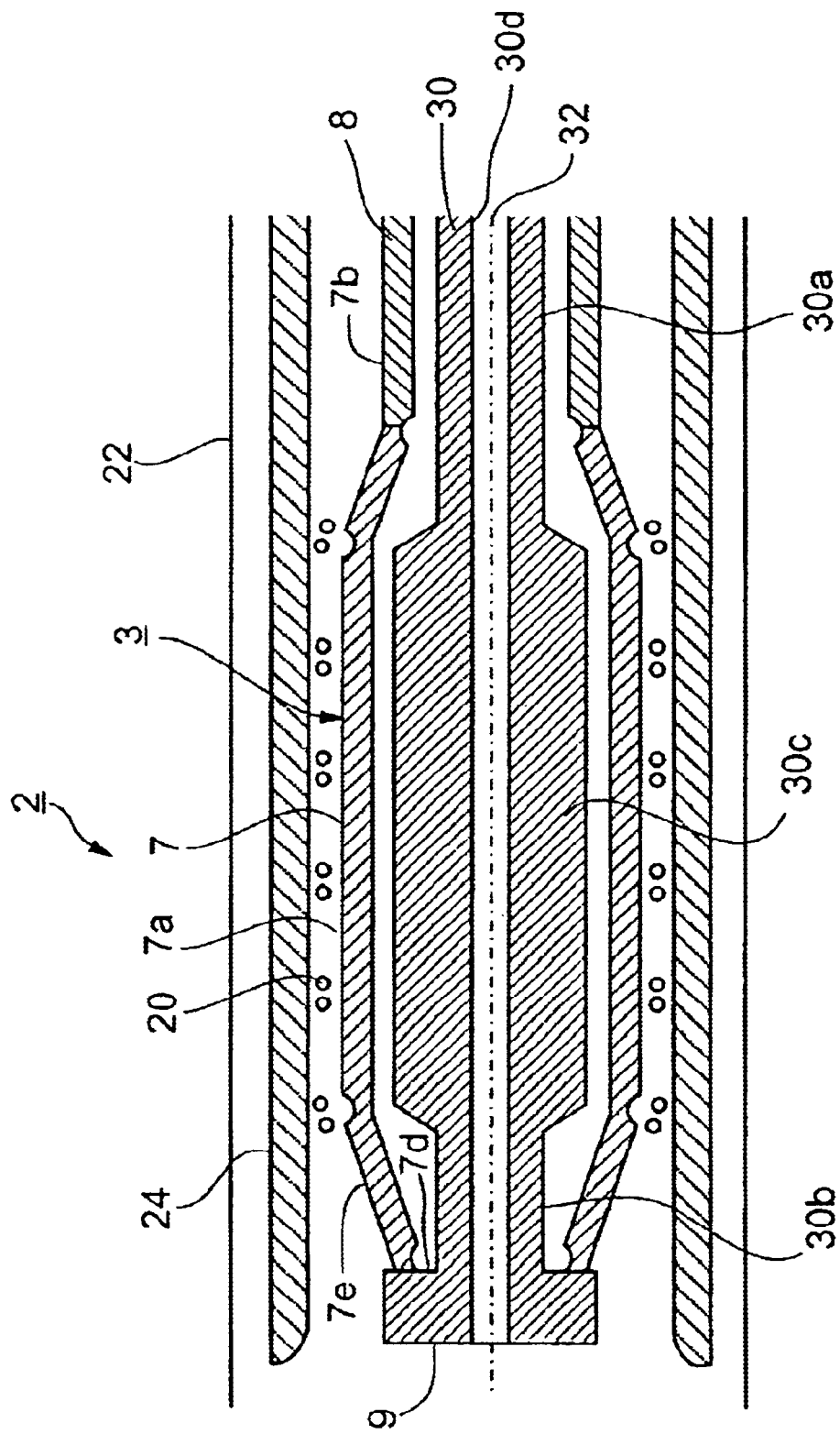
FIG. 3a schematically shows, in longitudinal cross-section, a delivery appliance constructed in accordance with the invention in its contracted state for introduction into the body lumen.

It is to be understood that the foregoing drawings, and the description below, are provided primarily for purposes of facilitating understanding the conceptual aspects of the invention and various possible embodiments thereof, including what is presently considered to be a preferred embodiment. In the interest of clarity and brevity, no attempt is made to provide more details than necessary to enable one skilled in the art, using routine skill and design, to understand and practice the described invention. It is to be further understood that the embodiments described are for purposes of example only, and that the invention is capable of being embodied in other forms and applications than described herein.

DESCRIPTION OF PREFERRED EMBODIMENTS

The delivery appliances illustrated in the drawings as preferred embodiments of the invention do not utilize expansion balloons, and therefore avoid many of the difficulties briefly described above in the use of such balloons, for delivering intraluminal devices, particularly intravascular devices, into a lumen of a subject's body. The delivery method is substantially the same as in traditional methods, except that the expansion and contraction of the delivery appliance is produced by effecting relative movement between mechanical elements, rather than by the expansion and contraction of a balloon. Accordingly, the description below will concern only the delivery appliance itself and the manner in which it is expanded and contracted when deploying the intravascular device, as the remainder of the deployment procedure would be substantially the same as when using the traditional expansion balloon.

The Embodiment of FIGS. 1a–3c

FIG. 1a illustrates the external appearance of the expandable part of a delivery appliance constructed in accordance with the present invention in its contracted state, whereas FIG. 1b illustrates it in its expanded state. The overall appliance, generally designated 2 in FIGS. 3a–3c, includes a tubular member 3 of elastic material, such as stiff plastic or metal, elongated along its longitudinal axis LA. Tubular member 3 is formed with a plurality of longitudinally-extending, circumferentially-spaced slits 4 terminating along circular lines 5, 6 at the opposite ends of the tubular member. Such a slitted tube thus defines an annular array of stiff supporting strips 7 interconnected together at the opposite ends of the tubular member outwardly of the circular lines 5 and 6.

The annular array of supporting strips 7 thus define an annular supporting surface for the expandable intraluminal device to be delivered; the end 8 of the tubular member outwardly of circular line 5 defines one end, namely the proximal end, of the annular array of supporting strips; and the opposite end 9, outwardly of circular line 6, defines the opposite end, in this case the distal end, of the annular array of supporting strips. As described below, each of the supporting strips 7 in the annular array is laterally deformable to radially expand or radially contract the annular array of supporting strips, and the annular supporting surface defined by them.

As shown particularly in FIGS. 2a and 2b, each of the supporting strips 7 is stiff in the longitudinal direction but is formed with four integral hinges 11, 12, 13, 14, which permit the strip to be deformed in the lateral direction, i.e., towards or away from the longitudinal axis LA. Integral hinges 11 and 12 at the opposite ends of the annular array are aligned with circles 5 and 6, respectively, defining the proximal and terminal ends of the annular array. Integral hinges 13 are aligned along a circular line at one end of the annular array, closer to the circular line of integral hinges 11; whereas the integral hinges 14 are aligned along another circular line at the opposite end, closer to the circular line of integral hinges 12.

FIGS. 2a and 2b illustrate the construction of each of the supporting strips 7. It includes a main central section 7a extending between the two central grooves 13, 14; an end section 7b defined by groove 11 at one end and joined to the central section 7a by a juncture section 7c between the two grooves 11 and 13; and an end section 7d defined by groove 12 at the opposite end joined to the central section 7a by a juncture section 7e between the two grooves 12 and 14.

As will be described more particularly below with respect to FIGS. 3a–3c, in the annular array of supporting strips 7 illustrated in FIGS. 1a and 2a, the central sections 7a of all the supporting strips 7 define a radially expandable and contractible annular supporting surface for supporting the expandable intraluminal device to be delivered by the illustrated appliance; end sections 7b define the proximal end of the annular array of supporting strips; and end sections 7d define the distal end of the annular array of supporting strips.

FIG. 2c more particularly illustrates the construction of integral hinge 14 between the central supporting section 7a of the supporting strip 7 and the coupling section 7e coupling it to the distal end section 7d. As shown particularly in FIG. 2c, integral hinge 14 is defined by a semi-circular groove extending transversely of the respective supporting strip 7, permitting the strip to be bent outwardly in the direction of the surface of the supporting strip formed with the groove. That is, when a force is applied to the supporting strip in the axial direction of the supporting strip, groove 14 permits the supporting strip to be deformed more easily in the direction of the surface formed with the groove 14 than in the opposite direction.

As seen particularly in FIG. 2b, groove 13 at the opposite end of the central supporting section 7a is also formed on the outer surface of the supporting strip 7 as groove 14, whereas the two end grooves 11 and 12 are formed on the inner surface of the supporting strip. Accordingly, when an axial force is applied to supporting strip 7 illustrated in FIG. 2a tending to move the proximal end 7b towards the distal end 7d, the supporting strip deforms laterally to the position illustrated in FIG. 2b, wherein the central section 7a of the supporting strip moves outwardly.

Thus, in the annular array of such supporting strips, such an axial force causes the annular surface defined by sections 7a of the array of supporting strips to be radially expanded; whereas the juncture sections 7c and 7e are deformed to inclined positions to couple the central sections 7a with the proximal sections 7b and distal sections 7d. When an axial force is applied to the supporting strips 7 in the opposite direction, i.e., tending to move the proximal sections 7b away from the distal sections 7d, the various sections of the supporting strips are deformed in the opposite direction to the condition illustrated in FIG. 2a.

It will be appreciated that during both the radial expansion and radial contraction of the annular array of supporting strips 7, the central supporting sections 7a always remain parallel to the longitudinal axis LA of the annular array; that is, they define a small-diameter cylindrical supporting surface when in their contracted positions as shown in FIG. 1a, and a large-diameter cylindrical supporting surface when in their expanded positions as shown in FIG. 1b.

Figure 3B:
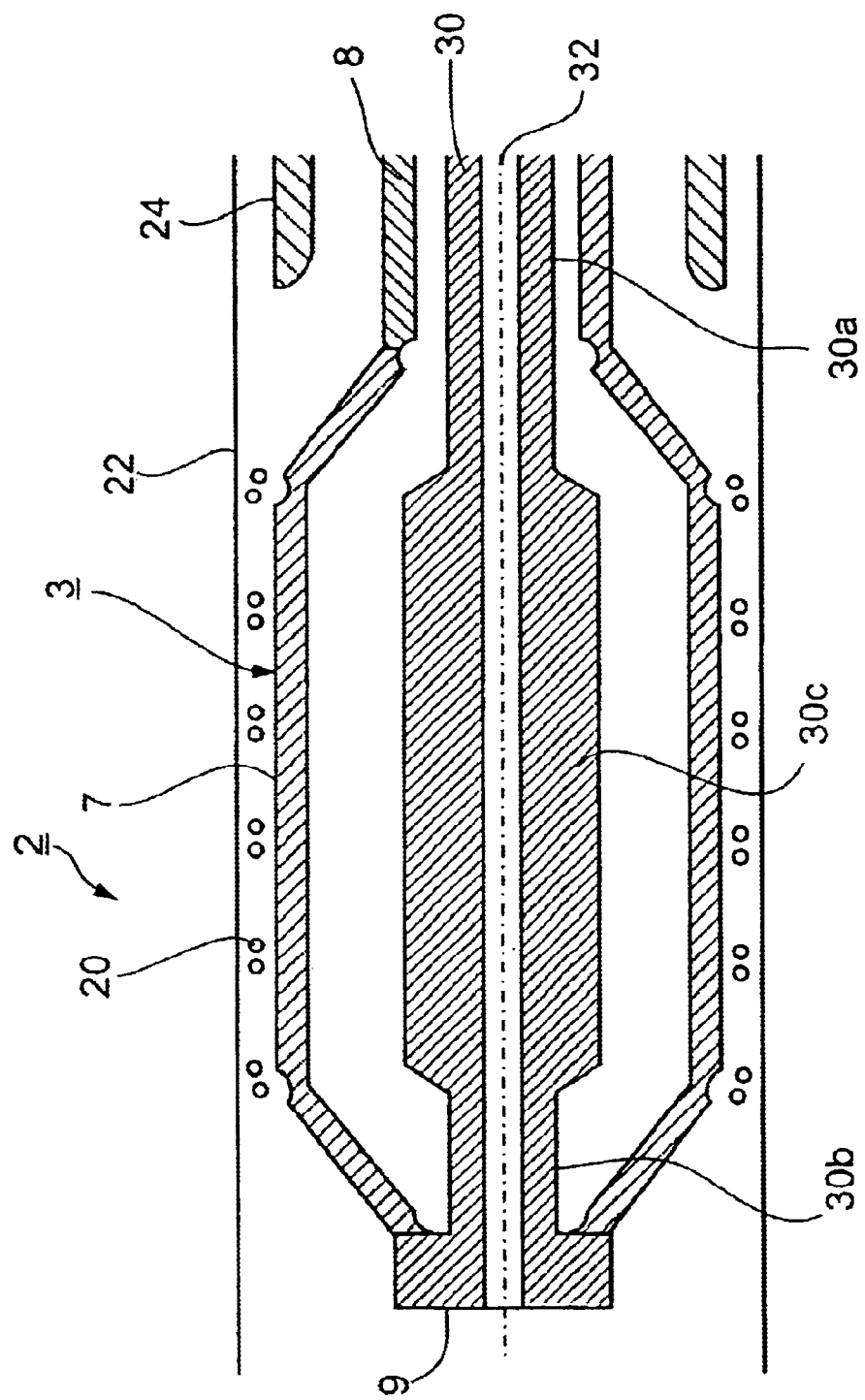
FIG. 3b is a view corresponding to that of FIG. 3a but showing the delivery appliance in its expanded state.
Figure 3C:
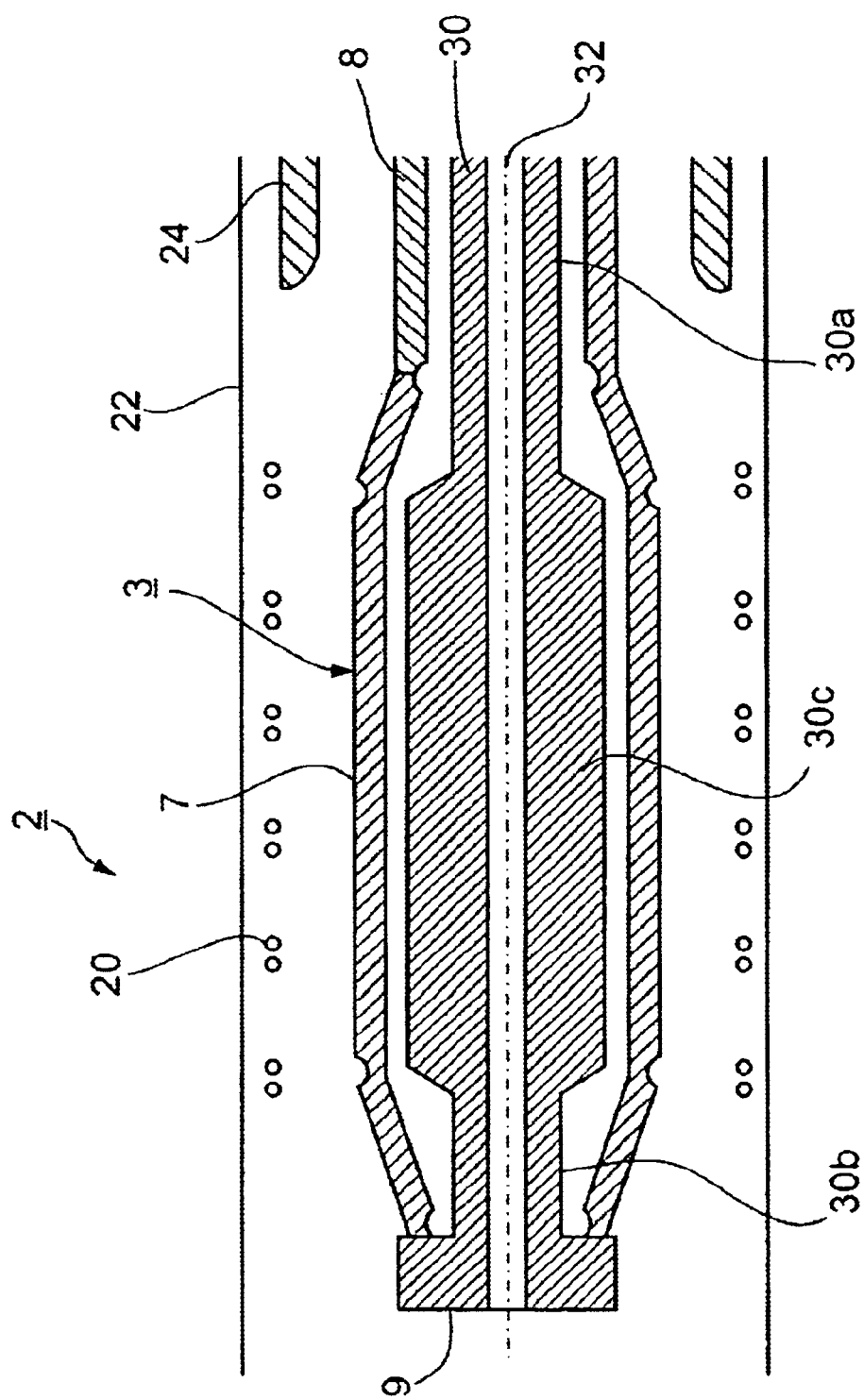
FIG. 3c is a view corresponding to that of FIG. 3a but showing the appliance returned to its contracted state for removal from the lumen, while the intravascular device remains anchored within the lumen.

FIG. 3a more particularly illustrates the contracted condition of the delivery appliance 2, and its annular array 3 of supporting strips 7, including the expandable intravascular device 20 received on the outer surfaces of the supporting strips 7 so as to be radially expanded by the lateral movements of the supporting strips to their expanded condition shown in FIG. 1b. Such an intravascular device 20 may be, for example, a stent to be deployed in firm engagement with the interior wall of a blood vessel lumen 22 by the expansion of the delivery appliance.

As shown in FIG. 3a, the delivery appliance 2 further includes an outer constraining sleeve 24 which is applied over the intravascular device 20 after the latter has been applied over the outer face of the annular array of supporting strips 7. The outer sleeve 24 is of an internal diameter to retain the delivery appliance 2, after being loaded with the intravascular device 20, in its contracted condition for movement through the lumen 22 to the desired location where the intravascular device 20 is to be deployed, at which time the outer sleeve 24 is removed for deploying the intravascular device.

As further shown in FIG. 3a, the delivery appliance 2 also includes an inner connecting stem 30 extending through the annular array of supporting strips 7. One end 30a of the connecting stem 30, at the proximal (right) end of the delivery appliance 2, passes through the proximal end 8 of the annular array of supporting strips 7 defined by the end sections 7b of the supporting strips, and is axially movable with respect that end of the supporting strips. The opposite end 30b of the connecting stem 30 is coupled, in any suitable manner as by heat-welding or adhesive, to the end sections 7d of the annular array of supporting strips 7 defining the distal end of the annular array, so as to be axially movable with such distal end sections of the supporting strips. The central section 30c of connecting stem 30, namely that section enclosed by the central supporting sections 7a of the annular array of supporting strips 7, is of increased thickness to increase the stiffness of the connecting stem when moved axially in one direction to radially expand the supporting sections 7a, or in the opposite direction to radially contract the supporting sections.

Connecting stem 30 is hollow, as shown at 30d, to allow it, and the complete delivery appliance including it, to be received on a guiding wire, shown schematically at 32. In the traditional balloon catheter system, such a guiding wire 32 is introduced into the lumen for guiding the balloon catheter, and the intravascular device carried thereby, to the desired location in the lumen where the intravascular device is to be implanted. The same guiding wire 32 may thus be used for guiding the delivery appliance 2 of the present invention, and the intravascular device carried thereby, to the desired location in the lumen for implantation therein.

OPERATION

The illustrated delivery appliance may be used in the following manner:

FIG. 3a shows the annular array 3 of supporting strips 7 in their contracted condition (corresponding to FIG. 1a) such that the outer surfaces of the intermediate sections 7a of the supporting strips 7 define an annular surface of small diameter for receiving the intravascular device 20 in its contracted condition. The outer constraining sleeve 24 is applied over the intravascular device 20 and thereby retains the delivery appliance 2 in its contracted condition with the intravascular device 20 interposed between the outer sleeve 24 and the outer surfaces of the supporting strips 7.

Before the delivery appliance 2, so-loaded with the intravascular device 20 and the outer constraining sleeve 24, is introduced into the lumen 22, a guiding wire 32 is introduced into the lumen and guided to the proper location in accordance with the usual methods used with balloon-type catheters. After the guiding wire 32 has been so introduced, the delivery appliance 2 is applied to the guiding wire, by passing the distal end 30b of the hollow stem 30 through the proximal end of the guiding wire 32.

The guiding wire is then used to guide the movement of the delivery appliance 2 to the desired location for deployment of the intravascular device 20.

The proximal end 30a of the connecting stem 30 is extended so as to be of sufficient length so as to be manipulateable externally of the patient's body receiving the intravascular implant. In the embodiment illustrated in FIGS. 3a–3c, the proximal end 8 of the tubular member defining the annular array of supporting strips 7 is also extended for manipulation externally of the patient's body. Similarly, the outer constraining sleeve 24 is also extended, or is otherwise connected to a device, for external manipulation.

When the delivery appliance 2 has been delivered to the proper location for deployment of the intravascular device 20, the outer constraining sleeve 24 is removed. The proximal end 30a of the stem 30 is then moved (rightwardly, FIG. 3a) to apply an axial compressional force to the annular array of supporting strips 7, and thereby to move the distal end 9 of the annular array of supporting strips 7 towards the proximal end 8. This movement of the opposite ends of the supporting strips 7 towards each other, deforms the supporting strips 7 laterally in the outward direction, as permitted by the integral hinges 11–14 of each of the supporting strips.

As described earlier, this arrangement of integral hinges causes the intermediate sections 7a of the supporting strips 7 to move outwardly, while maintaining substantial parallel relationship to the longitudinal axis LA occupied by the guiding wire 32. The intravascular device 20 supported on the outer surfaces of the supporting strips 7 is thus expanded into a firm engagement with the walls of the lumen 22, as shown in FIG. 3b.

In order to remove the delivery appliance 2 from the lumen, the proximal end 30a of the connecting stem 30 is moved in the opposite direction (leftwardly, FIGS. 3a, 3b) i.e., to apply an axial extension force to the annular array of supporting strips 7, and to thereby move the distal end 9 of the annular array 3 of supporting strips 7 away from the proximal end 8. This causes the supporting strips 7 to be deformed laterally inwardly towards the longitudinal axis LA of the delivery appliance, i.e., radially contracting the diameter defined by the outer surfaces of the supporting strips. This permits the delivery appliance 2 to be removed from the lumen 22 while the intravascular device 20 is retained within the lumen, as shown in FIG. 3c.

The tubular member defining the supporting strips 7 may be made of any suitable elastic material, such as plastic, metal, or a combination of plastic and metal, providing stiffness in the longitudinal direction, but permitting deformation in the lateral direction by the integral hinges 11–14 formed in the strips as described above. The expandable intravascular device 24 may be of any known type and constructed of known materials, such as described, for example, in International Patent Application PCT/IL01/00624 by the same Applicant, the contents of which are incorporated herein by reference.

The Embodiment of FIGS. 4a–4d

FIGS. 4a–4d illustrate another embodiment of the invention wherein the delivery appliance, therein generally designated 40, is moved by means of a spring to its expanded condition for deploying the intravascular device after the delivery appliance has been moved to the proper location and the constraining outer sleeve removed. It will thus be seen that, in this embodiment, the proximal end 8 of the tubular member defining the annular array of supporting strips 7 need not be extended for manipulation externally of the patient's body. Except for this difference, as well as some other minor modifications as will be described more fully below, the delivery appliance 40 illustrated in FIGS. 4a–4d is generally of the same construction as delivery appliance 2 illustrated in FIGS. 1a–3c, and therefore, for the sake of brevity, the same reference numerals have been used for identifying corresponding parts.

In the delivery appliance 40 illustrated in FIGS. 4a–4d, the proximal end 8' of the tubular member defining the annular supporting strips 7 is not extended so as to be externally of the patient's body as briefly described above, but rather is formed with an annular rib 8a on its inner surface at the proximal end of the tubular member, and with a second annular rib 8b on its inner surface inwardly of annular rib 8a. The two ribs 8a, 8b thus define axially-spaced annular shoulders on the inner face of proximal end 8 of the tubular member.

Figure 4A:
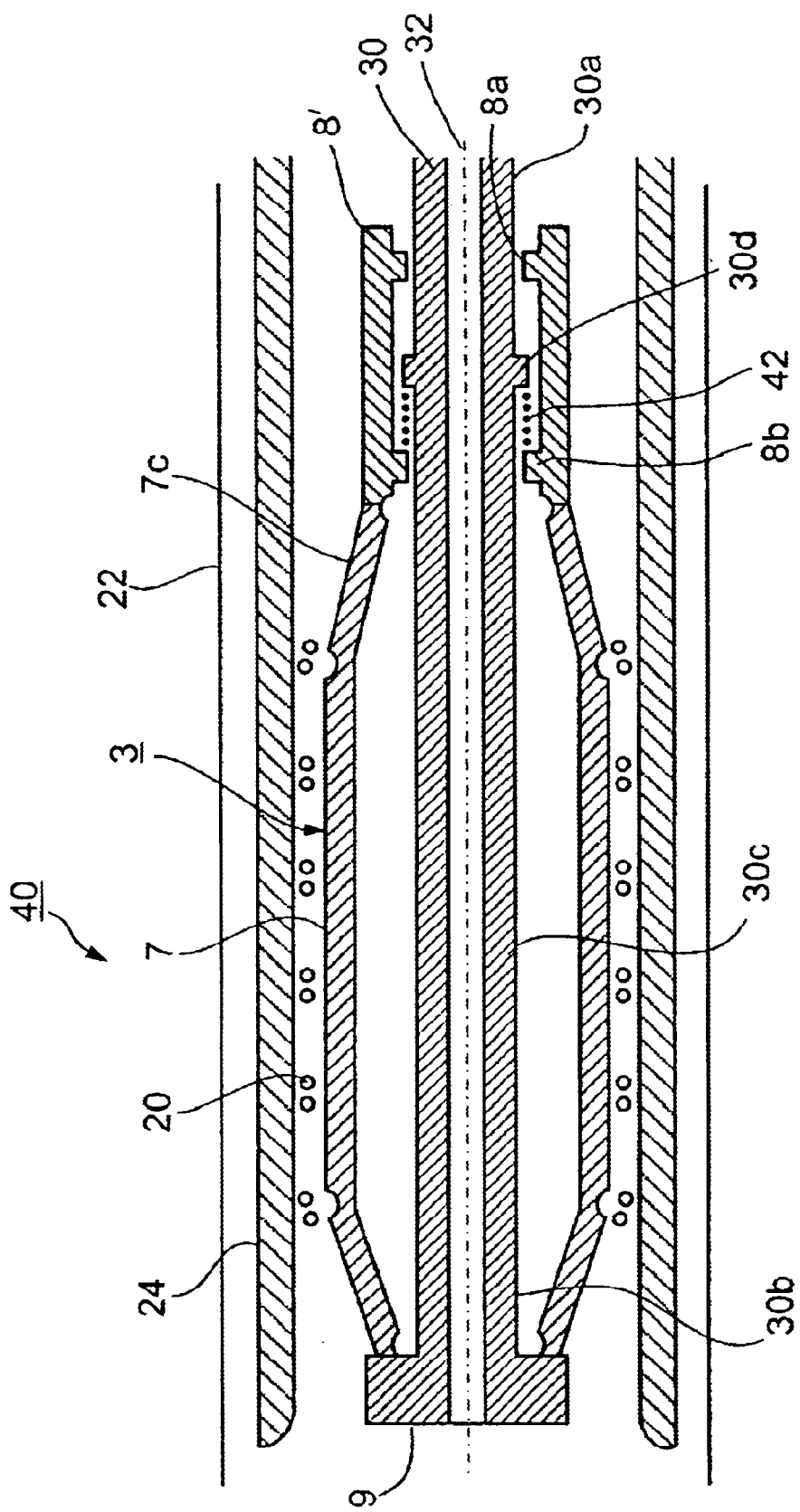
FIGS. 4a and 4b are views corresponding to FIGS. 3a and 3b but illustrating another delivery appliance constructed in accordance with the present invention.

In addition, the proximal end 30a of the inner stem 30 is formed on its outer surface with an annular rib 30d defining an annular shoulder between the two annular shoulders 8a, 8b. A compression spring 42 is interposed between annular shoulder 30d and annular shoulder 8b at the proximal end 8' of the tubular member. Thus, in the contracted condition of the delivery appliance 40, as shown in FIG. 4a, with the intravascular device 20 applied over the outer surfaces of the supporting elements 7 and the outer constraining sleeve 24 applied thereover, spring 42 is under compression.

Figure 4B:
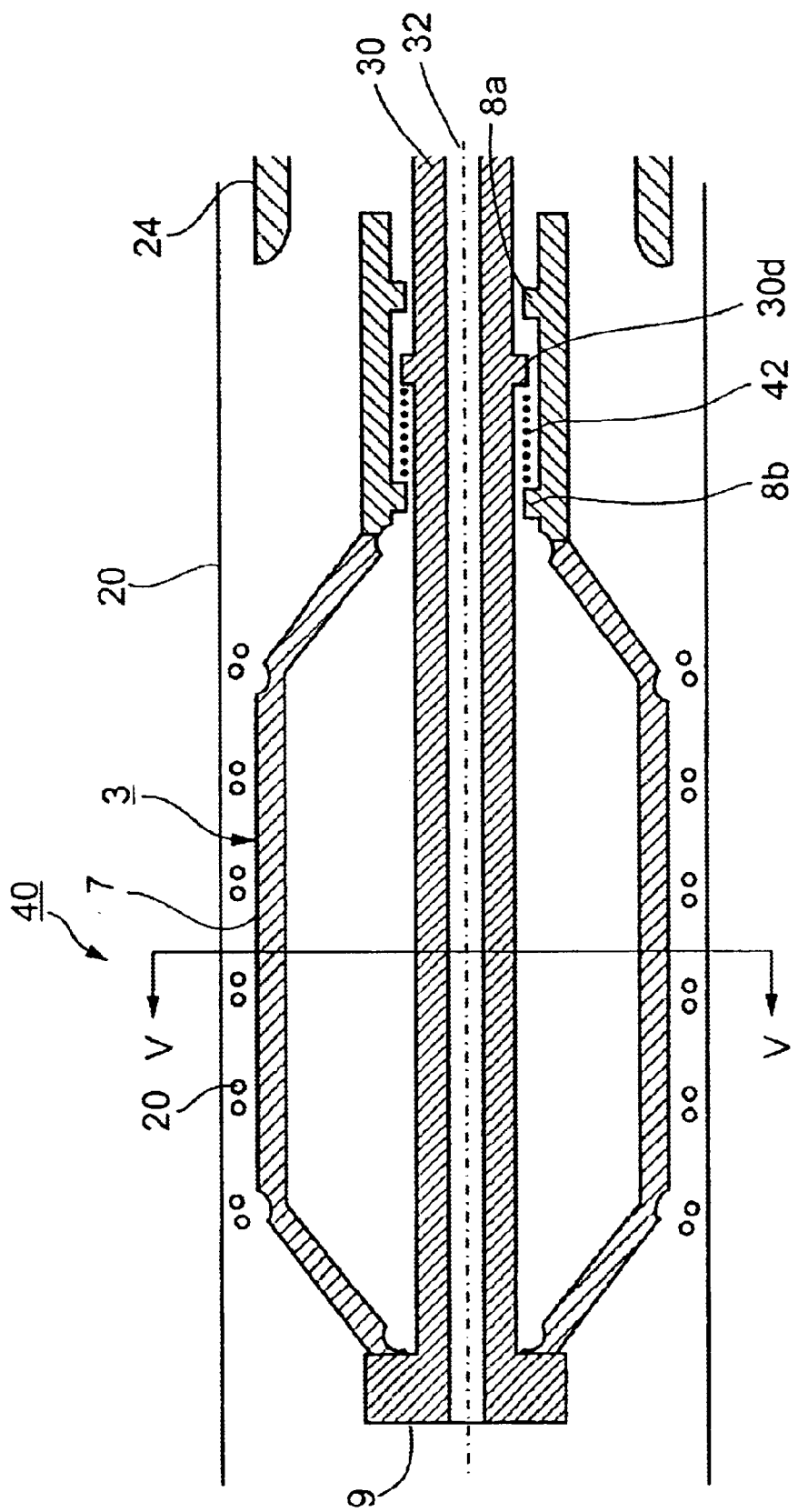

The delivery appliance 40 in this condition, with the spring 42 under compression, is delivered through the patient's lumen to the implantation site, whereupon the constraining sleeve 24 is removed, as described above. As soon as the constraining sleeve 24 is removed, spring 42 expands and automatically moves the proximal end 30a of stem 30 outwardly of the proximal end 8' of the supporting strips 7, thereby moving the opposite end 8', 9 of the annular array of supporting strips 7 towards each other. This movement axially compresses the supporting strips 7 and thereby deforms them laterally outwardly in the same manner as described above with respect to FIGS. 3a–3, to deploy the intravascular device 20 against the inner wall of the lumen 22 as shown in FIG. 4b.

Figure 4C:
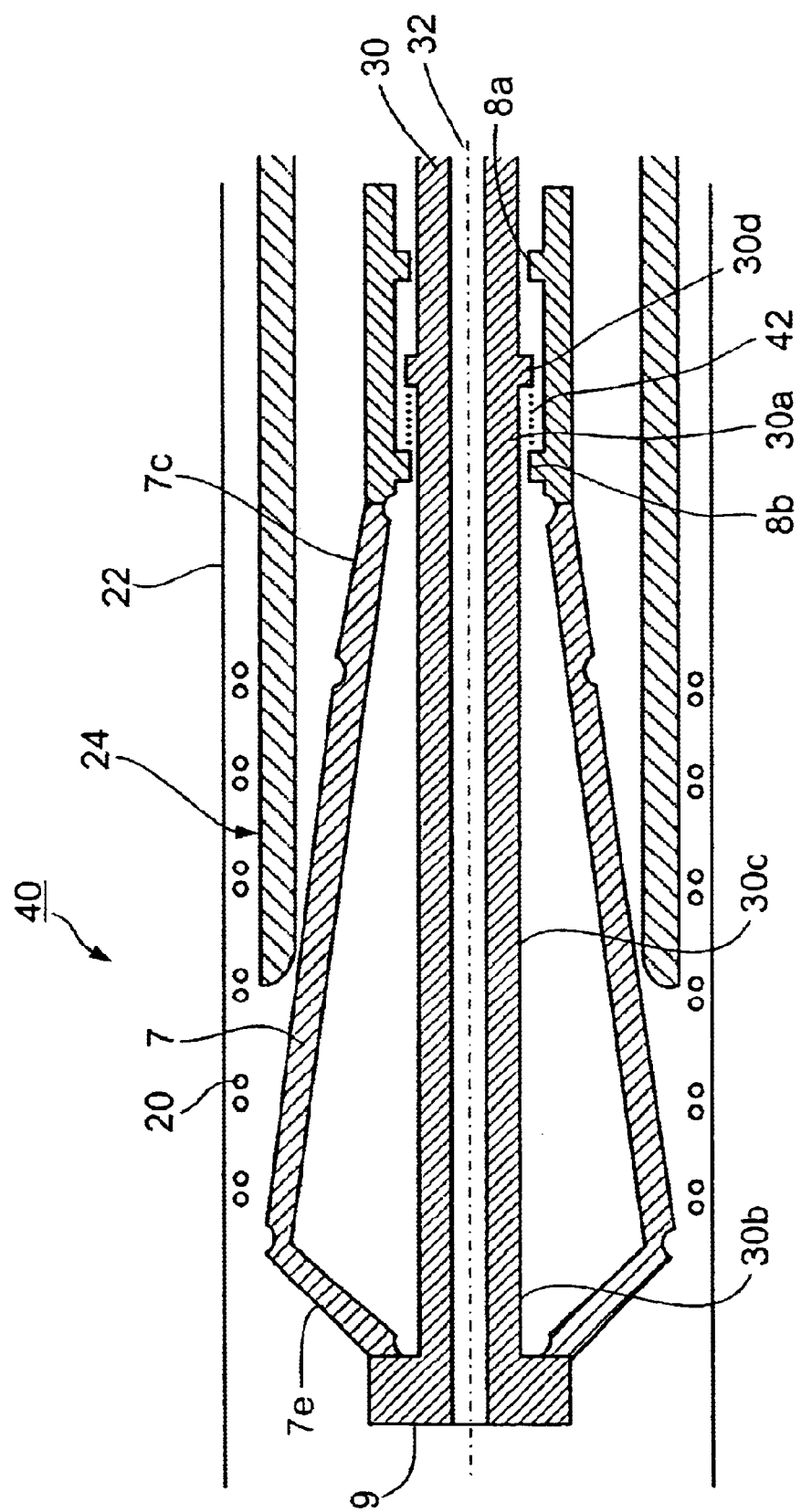
FIG. 4c illustrates the delivery appliance of FIGS. 4a and 4b after the intravascular device has been deployed and while the outer sleeve is being re-applied over the delivery appliance for removing it from the lumen.
Figure 4D:
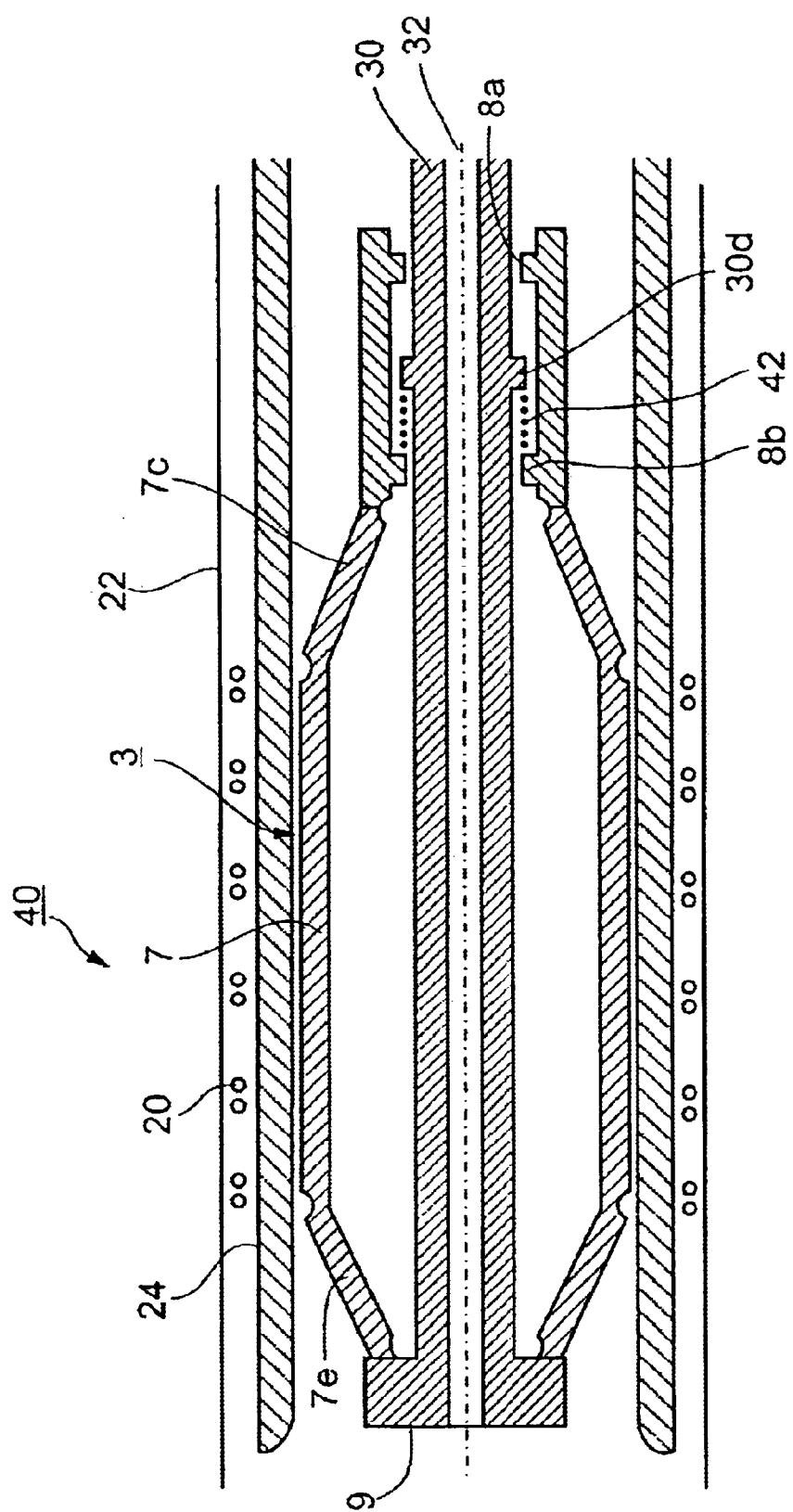
FIG. 4d is a view similar to that of FIG. 4c, but showing the appliance after the outer sleeve has been completely applied.

FIG. 4c illustrates the re-application of the constraining sleeve 24 to the outer surfaces of the supporting strips 7 in order to laterally deform them inwardly towards the longitudinal axis of the delivery appliance; and FIG. 4d illustrates the condition of the delivery appliance 40 after the constraining has been fully applied, to thereby permit removal of the delivery appliance 40 from the lumen 22.

Figure 5:
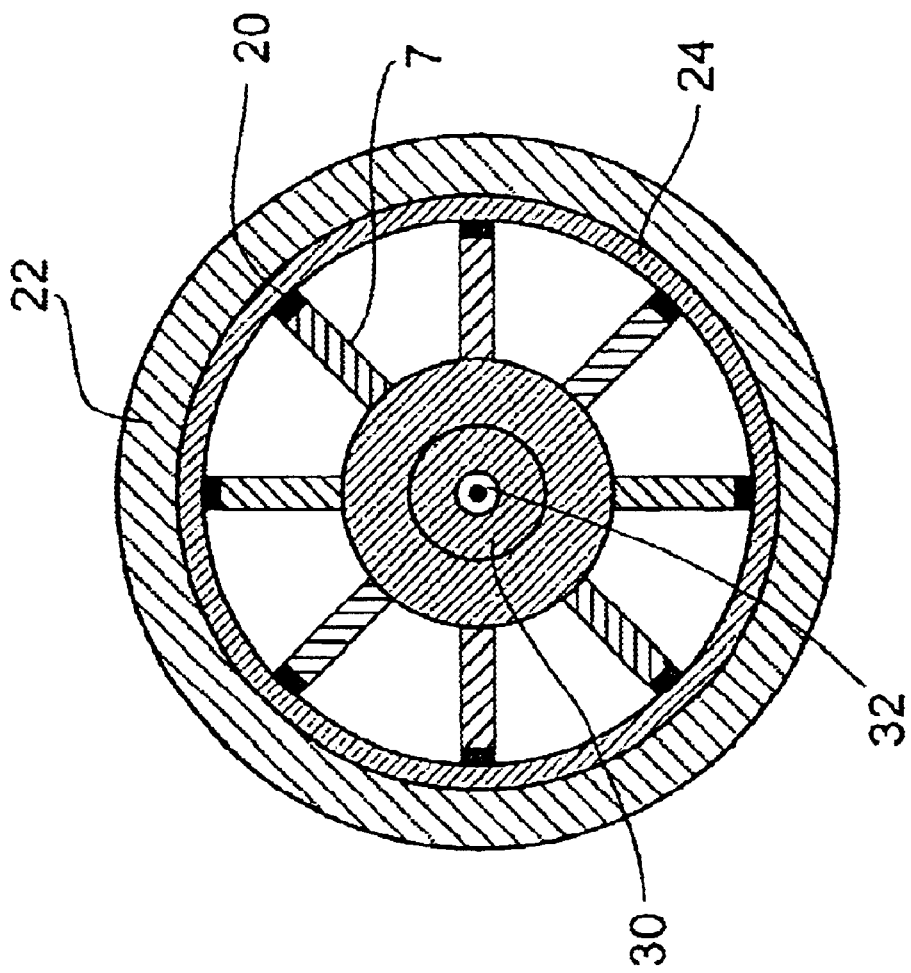
FIG. 5 schematically shows a transverse cross-section, taken along line V—V of FIG. 4b, after the delivery appliance has been expanded to deploy the intravascular device at the desired location in the lumen.

FIG. 5 illustrates the cross-section of the delivery appliance 40 of FIGS. 4*a*–4*d*, (as well as that of appliance 2 of FIGS. 1*a*–3*c*) in the expanded condition of the delivery appliance, at the time the annular array of supporting strips is radially expanded to press the intravascular device 20 firmly against the inner wall of the lumen 22. As shown in FIG. 5, even at this time, a flow passageway is maintained through the delivery device so as to avoid the hazards of balloon-type delivery devices blocking the flow of the blood. Thus, the described arrangement of integral hinges formed in each of the supporting strips 7 causes the supporting strips to move outwardly, parallel to the longitudinal axis of the delivery appliance, thereby maintaining the flow passageway through the delivery appliance. It also better assures a firm engagement of the intravascular device against the inner wall of the lumen even when used in relatively large-size lumens.

While the invention has been described with respect to two preferred embodiments, it will be appreciated that these are set forth merely for purposes of example. Thus, the intraluminal device could be of the self-expansible-type such that it self automatically expands upon the removal of the outer constricting sleeve, or could be of the type which is expanded by the axial compressional force applied to the opposite ends of the tubular member defining the annular array of supporting strips 7. In addition, the annular array of supporting strips 7 could be constructed of individual strips joined together at their proximal and distal ends, or could be provided with a different construction of integral hinges. Further, other arrangements of integral hinges could be used so as to define a plurality of discrete axially-spaced annular supporting surfaces, rather than a single continuous annular supporting surface, particularly where the intraluminal device to be applied is relatively long. Also, the invention could be used in other medical applications, for delivering other types of expandable devices to desired locations in lumens, and could also be used in non-medical applications for the application of devices to lumens or other tubular passageways.

Many other variations, modifications and applications of the invention will be apparent.

What is claimed is:

1. A delivery appliance for delivering an expandable annular device to a desired location in a lumen, comprising:

an annular array of supporting strips extending from a proximal end of the annular array to a distal end of the annular array, to define an annular supporting surface for said expandable annular device, each of said supporting strips being laterally deformable to radially expand or radially contract said annular array and said annular supporting surface defined thereby, each of said supporting strips in said annular array being formed with at least one integral hinge at the proximal end of the annular array and with at least one integral hinge at the distal end of the annular array, such that the intermediate portion between said at least one integral hinge at the proximal end and said at least one integral hinge at the distal end of each of said supporting strips remain substantially parallel to the longitudinal axis of the annular array during the radial contraction and the radial expansion of the annular supporting surface defined by said supporting strips;

and a connecting stem passing through said annular array of supporting strips;

said connecting stem having a distal end coupled to said supporting strips at the distal end of the annular array for axial movement therewith, and a proximal end passing through the proximal end of the annular array of supporting strips for axial movement with respect thereto;

said proximal end of the connecting stem being axially movable in one direction to move said distal end of the annular array axially away from said proximal end of the annular array to radially contract said annular supporting surface;

said proximal end of the connecting stem being axially movable in the opposite direction to move said distal end of the annular array axially towards said proximal end of the annular array to radially expand said annular supporting surface.

2. The delivery appliance according to claim 1, wherein each of said supporting strips in the annular array is stiff in the longitudinal direction.

3. The delivery appliance according to claim 2, wherein each of said supporting strips includes a strip of stiff material extending from said proximal end of the annular array to said distal end of the annular array and formed with at least one transversely-extending groove producing one of said at least one integral hinge at said proximal end and said at least one integral hinge at said distal end.

4. The delivery appliance according to claim 3, wherein said transversely-extending groove is formed on one surface of said strip of stiff material to permit said strip to be laterally deformed more easily in the direction of said surface than in the opposite direction.

5. The delivery appliance according to claim 4, wherein said groove is of a semi-circular configuration.

6. The delivery appliance according to claim 1, wherein each of said supporting strips in the annular array is formed with two integral hinges at the proximal end of the annular array, and with two integral hinges at the distal end of the annular array.

7. The delivery appliance according to claim 1, wherein the delivery appliance further includes an outer sleeve receiving the annular array of supporting strips when the annular array is in its contracted condition to maintain them in its contracted condition until the outer sleeve is removed from the annular array of supporting strips.

8. The delivery appliance according to claim 7, wherein said expandable annular device is interposed between said outer sleeve and said annular array of supporting strips when said annular array is in its contracted condition.

9. The delivery appliance according to claim 8, wherein the proximal end of the stem, and the proximal end of the annular array of supporting strips are both extended outwardly in the proximal direction to enable said proximal ends of the stem and of the annular array of supporting strips to be manually grasped in order to effect said axial movement in said one direction or in said opposite direction.

10. The delivery appliance according to claim 8, wherein a spring is interposed between said proximal end of the stem and said proximal end of the annular array of supporting strips urging said proximal ends apart, such that removal of the outer sleeve causes said spring automatically to effect said axial movement in said opposite direction to expand said inner supporting surface and thereby the annular device supported thereon.

11. The delivery appliance according to claim 1, wherein said annular array of supporting strips is constituted of a tubular member of elastic material formed with a plurality of longitudinally-extending circumferentially-spaced slits terminating short of the opposite ends of the tubular member, such that the slitted tubular member defines said annular array of supporting strips, and said opposite ends of the tubular member define said proximal and distal ends, respectively, of said annular array.

12. The delivery appliance according to claim 1, wherein said annular array of supporting strips are constructed and dimensioned for delivering an expandable intraluminal device to a desired location in a lumen of a subject's body.

13. The delivery appliance according to claim 12, wherein said supporting strips of the annular array are constructed and dimensioned for delivering an expandable intravascular device to a desired location in the vascular system of a subject's body.

14. A delivery appliance for delivering an expandable intravascular device to a desired location in a lumen, comprising:
   an annular array of supporting strips dimensioned to receive said expandable intravascular device and extending from a proximal end of the annular array to a distal end of the annular array, to define an annular supporting surface for said expandable intravascular device, each of said supporting strips being laterally deformable to radially expand or radially contract said annular array of supporting strips, and said annular supporting surface defined thereby, each of said supporting strips in said annular array being formed with at least one integral hinge at the proximal end of the annular array and with at least one integral hinge at the distal end of the annular array, such that the intermediate portion between said at least one integral hinge at the proximal end and said at least one integral hinge the distal end of each of said supporting strips remain substantially parallel to the longitudinal axis of the annular array during the radial contraction and the radial expansion of the annular supporting surface defined by said supporting strips;
   and a connecting stem passing through said annular array of supporting strips;
   said connecting stem having a distal end coupled to said supporting strips at the distal end of the annular array for axial movement therewith, and a proximal end passing through the proximal end of the annular array of supporting strips for axial movement with respect thereto;
   said proximal end of the connecting stem being axially movable in one direction to move said distal end of the annular array axially away from said proximal end of the annular array to radially contract said annular supporting surface, and thereby to permit the intravascular device to be received thereon, to be delivered via the lumen to a desired location therein, and to be removed from the lumen after delivering the intravascular device to said desired location therein;
   said proximal end of the connecting stem being axially movable in the opposite direction to move said distal end of the annular array axially towards said proximal end of the annular array to radially expand said annular supporting surface and said intravascular device supported thereon.

15. The delivery appliance according to claim 14, wherein each of said supporting strips in the annular array is stiff in the longitudinal direction.

16. The delivery appliance according to claim 15, wherein each of said supporting strips includes a strip of stiff material extending from said proximal end of the annular array to said distal end of the annular array and formed with at least one transversely-extending groove producing one of said at least one integral hinge at said proximal end and said at least one integral hinge at said distal end.

17. The delivery appliance according to claim 16, wherein said transversely-extending groove is formed on one surface of said strip of stiff material to permit said strip to be laterally deformed more easily in the direction of said a surface than in the opposite direction.

18. The delivery appliance according to claim 17, wherein said groove is of a semi-circular configuration.

19. The delivery appliance according to claim 14, wherein each of said supporting strips in the annular array is formed with two integral hinges at the proximal end of the annular array, and with two integral hinges at the distal end of the annular array.

20. The delivery appliance according to claim 14, wherein the delivery appliance further includes an outer sleeve receiving the annular array of supporting strips when the annular array is in its contracted condition to maintain them in its contracted condition until the outer sleeve is removed from the annular array of supporting strips.

21. The delivery appliance according to claim 20, wherein said expandable annular device is interposed between said outer sleeve and said annular array of supporting strips when said annular array is in its contracted condition.

22. The delivery appliance according to claim 21, wherein the proximal end of the stem and the proximal end of the annular array of supporting strips both extend outwardly in the proximal direction to enable said proximal ends of the stem and of the annular array of supporting strips to be manually grasped in order to effect said axial movement in said one direction or in said opposite direction.

23. The delivery appliance according to claim 21, wherein a spring is interposed between said proximal end of the stem and said proximal end of the annular array of supporting strips urging said proximal ends apart, such that removal of the outer sleeve causes said spring automatically to effect said axial movement in said opposite direction to expand said inner supporting surface and thereby the annular device supported thereon.

24. The delivery appliance according to claim 14, wherein said annular array of supporting strips is constituted of a tubular member of elastic material formed with a plurality of longitudinally-extending circumferentially-spaced slits terminating short of the opposite ends of the tubular member, such that the slitted tubular member defines said annular array of supporting strips, and said opposite ends of the tubular member define said proximal and distal ends, respectively, of said annular array.

25. A delivery appliance for delivering an expandable annular device to a desired location in a lumen, comprising:
   an annular array of supporting strips extending from a proximal end of the annular array to a distal end of the annular array, to define an annular supporting surface for said expandable annular device, each of said supporting strips being laterally deformable to radially expand or radially contract said annular array and said annular supporting surface defined thereby;
   a connecting stem passing through said annular array of supporting strips;
   said connecting stem having a distal end coupled to said supporting strips at the distal end of the annular array for axial movement therewith, and a proximal end passing through the proximal end of the annular array of supporting strips for axial movement with respect thereto;
   said proximal end of the connecting stem being axially movable in one direction to move said distal end of the annular array axially away from said proximal end of the annular array to radially contract said annular supporting surface;

said proximal end of the connecting stem being axially movable in the opposite direction to move said distal end of the annular array axially towards said proximal end of the annular array to radially expand said annular supporting surface;

an outer sleeve receiving the annular array of supporting strips when the annular array is in its contracted condition to maintain them in its contracted condition until the outer sleeve is removed from the annular array of supporting strips;

wherein said expandable annular device is interposed between said outer sleeve and said annular array of supporting strips when said annular array is in its contracted condition; and a spring interposed between said proximal end of the stem and said proximal end of the annular array of supporting strips said spring urging said proximal ends apart, such that removal of the outer sleeve causes said spring automatically to effect said axial movement in said opposite direction to expand said inner supporting surface and thereby the annular device supported thereon.

* * * * *